United States Patent
Ryuno et al.

(10) Patent No.: US 6,955,911 B2
(45) Date of Patent: Oct. 18, 2005

(54) METHOD OF CULTURING MICROORGANISM

(75) Inventors: Koichiro Ryuno, Kanagawa (JP); Etsuko Kobayashi, Kanagawa (JP)

(73) Assignee: Mitsubishi Rayon Co., Ltd., Tokyo (JP)

(*) Notice: Subject to any disclaimer, the term of this patent is extended or adjusted under 35 U.S.C. 154(b) by 473 days.

(21) Appl. No.: 10/221,200

(22) PCT Filed: Mar. 21, 2001

(86) PCT No.: PCT/JP01/02232

§ 371 (c)(1),
(2), (4) Date: Sep. 23, 2002

(87) PCT Pub. No.: WO01/70936

PCT Pub. Date: Sep. 27, 2001

(65) Prior Publication Data

US 2003/0068789 A1 Apr. 10, 2003

(30) Foreign Application Priority Data

Mar. 21, 2000 (JP) .................................. 2000-078484

(51) Int. Cl.$^7$ .............................. C12P 13/02; C12N 1/20
(52) U.S. Cl. .................... 435/253.6; 435/129; 435/244; 435/252.3
(58) Field of Search ................................ 435/129, 244, 435/252.3, 253.6

(56) References Cited

U.S. PATENT DOCUMENTS

| | | | |
|---|---|---|---|
| 5,089,411 A | * 2/1992 | Yamada et al. | ............. 435/244 |
| 5,318,908 A | 6/1994 | Seki et al. | |
| 5,334,519 A | * 8/1994 | Yamada et al. | ............. 435/129 |
| 5,705,382 A | 1/1998 | Endo et al. | |
| 5,807,730 A | 9/1998 | Ito et al. | |
| 6,132,985 A | * 10/2000 | Pierce | ......................... 435/29 |
| 6,444,451 B1 | * 9/2002 | Robins et al. | .............. 435/129 |

FOREIGN PATENT DOCUMENTS

| | | |
|---|---|---|
| EP | 0 307 926 | 3/1989 |
| EP | 307926 | 3/1989 |
| EP | 0 362 829 | 4/1990 |
| JP | 64-74996 | 3/1989 |
| JP | 2-000470 | 1/1990 |
| JP | 2-100674 | 4/1990 |
| JP | 8-38163 | 2/1996 |
| JP | 8-112089 | 5/1996 |

OTHER PUBLICATIONS

Toru Nagasawa et al.: "Optimum culture conditions for the production of cobalt–containing nitrile hydratase by Rhodococcus rhodochrous J1" Applied Microbiology and Biotechnology, vol. 34, No. 6, pp. 783–788 Mar. 1991.
Patent Abstracts of Japan, JP 8–038163, Feb. 13, 1996.
T. E. Leonova, et al., Applied Biochemistry and Biotechnology, vol. 88, No. 1–3, XP–009027439, pp. 231–241, "Nitrile Hydratase of Rhodococcus: Optimization of Synthesis in Cells and Industrial Applications for Acrylamide Production", Jul. 2000.
A. S. Yanenko, et al., Proceedings of the Ninth Symposium on the Actinomycetes, No. 7–8, XP–009027441, pp. 139–144, "Regulation of Nitrile Utilization in Rhodococcus", 1995.

* cited by examiner

*Primary Examiner*—Herbert J. Lilling
(74) *Attorney, Agent, or Firm*—Oblon, Spivak, McClelland, Maier & Neustadt, P.C.

(57) ABSTRACT

In cultivating a microorganism having nitrile hydratase production ability, by allowing at least one of a ketose, such as fructose, and a sugar alcohol, such as mannitol, to be present, growth inhibition by cobalt ion is prevented, thereby achieving cultivation at a high concentration and with a high activity.

5 Claims, No Drawings

METHOD OF CULTURING MICROORGANISM

TECHINICAL FIELD

The present invention relates to a method of producing culture microbial cells having high nitrile hydratase enzyme activity within a short period and at a high yield.

BACKGROUND ART

In recent years, from the viewpoint of energy conservation, renewed activity has been seen in attempts to utilize microorganisms or their enzymes as a biocatalyst for matter production. Nitrile hydratase is known as an enzyme which hydrates nitriles to thereby produce the corresponding amides. In particular, it is useful as a catalyst to produce acrylamide from acrylonitrile.

As microorganisms having nitrile hydratase production ability, for example, there are known bacteria belonging to genus *Nocardia* [see Japanese Patent Application Laying-Open (kokai) No. 54-129190], genus *Rhodococcus* [see Japanese Patent Application Laying-Open (kokai) No. 2-470], genus *Rhizobium* [see Japanese Patent Application Laying-Open (kokai) No. 5-236977], genus *Klebsiera* [Japanese Patent Application Laying-Open (kokai) No. 5-30982], genus *Aeromonas* [Japanese Patent Application Laying-Open (kokai) No. 5-30983], genus *Agrobacterium* [Japanese Patent Application Laying-Open (kokai) No. 8-154691], genus *Bacillus* [Japanese Patent Application Laying-Open (kokai) No. 8-187092], genus *Pseudonocardia* [Japanese Patent Application Laying-Open (kokai) No. 8-56684], and the like. In each of the above-mentioned publications, a method of cultivating microorganisms which produce nitrile hydratase activity is described.

Further, with respect to use of carbon source in cultivating, it is described in the section "Effect of carbon sources" of Applied Microbiology and Biotechnology (1991) 34:783–788 that "in producing nitrile hydratase by use of *R. rhodochroits* J1, the most suitable carbon source is 2% glucose."

DISCLOSURE OF THE INVENTION

None of the methods described in the above-mentioned publications are industrially practical as a method of obtaining culture microbial cells having nitrile hydratase activity within a short period and at a high yield.

For the purpose of enzyme induction, cobalt ions are added to culture solution according to the method described in Japanese Patent Application Laying-Open (kokai) No. 2-470, though it is difficult by employing such cobalt ion concentration to always effect stable obtainment of culture microbial cells having nitrile hydratase enzyme activity within a short period and at a high yield. Further, addition of a large amount of cobalt ions to the medium will cause remarkable growth inhibition, and, on the contrary, it is not possible to obtain culture microbial cells having nitrile hydratase activity within a short period and at a high yield.

In addition, in order to obtain culture microbial cells having nitrile hydratase activity within a short period and at a high yield, glucose or sucrose is considered preferable as a carbon source, and use of ketoses such as fructose or sugar alcohols such as mannitol has conventionally been considered scientifically impossible.

The object of the present invention is to provide a method of obtaining culture microbial cells having nitrile hydratase activity within a short period and at a high yield which solves the above problems.

The present inventors have conducted intensive studies on culture conditions to industrially obtain microbial cells having nitrile hydratase activity within a short period and at a high yield. As a result, the inventors found it possible to obtain highly active microbial cells as well as to reduce growth inhibition even in the presence of a large amount of cobalt ions in culture solution by allowing the presence of a ketose, e.g. fructose, and/or a sugar alcohol, e.g. mannitol, in the culture solution. Thus, the present invention has been accomplished.

Namely, the present invention is a method of cultivating a microorganism having nitrile hydratase production ability in a medium substrate containing a sugar alcohol and/or ketose, and a cobalt ion. Herein, the cobalt ion concentration is preferably 15 mg/L or more in terms of $CoCl_2$. Additionally, the sugar alcohol is preferably represented by the following general formula (I):

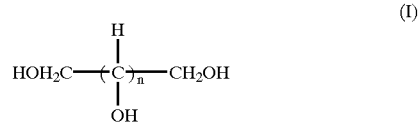

(I)

wherein n represents an integer from 2 to 4.

Furthermore, the ketose is represented by the following general formula (II):

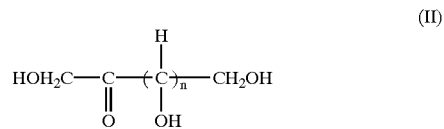

(II)

wherein n represents 3.

According to the present invention, a sugar alcohol and/or a ketose are used as a carbon source. However, it is not conventionally known that the presence of these sugar compounds in a culture solution allows the reduction of growth inhibition attributable to cobalt ion.

The present invention will hereinafter be described in detail.

The microorganisms of interest according to the present invention are not particularly limited, as long as they have nitrile hydratase production ability. Specifically, preferable examples of the microorganisms include *Nocardia* sp. N-775 described in Japanese Patent Examined Publication (kokoku) No. 56-17918, *Rhodococcus rhodochrous* J-1 described in Japanese Patent Examined Publication (kokoku) No. 06-55148, *Klebsiella* sp. MCI2609 described in Japanese Patent Application Laying-Open (kokai) No. 05-30982, *Aeromonas* sp. MCI2614 described in Japanese Patent Application Laying-Open (kokai) No. 05-30983, *Citrobacter freundii* MCI2615 described in Japanese Patent Application Laying-Open (kokai) No. 05-30984, *Agrobacterium rhizogenes* IAM13570 and *Agrobacterium tumefaciens* described in Japanese Patent Application Laying-Open (kokai) No. 05-103681, *Xanthobacter flavas* JCM1204 described in Japanese Patent Application Laying-Open (kokai) No. 05-161495, *Erwinia nigrifluens* MAFF03-01435, *Enterobacter* sp. MCI2707 described in Japanese Patent Application Laying-Open (kokai) No. 05-236975, *Streptomyces* sp. MCI2691 described in Japanese Patent Application Laying-Open (kokai) No. 05-236976, *Rhizobium* sp. MCI2610, *Rhizobium* sp. MCI2643, *Rhizobium loti*

IAM13588, *Rhizobium legminosarum* IAM12609 and *Rhizobium merioti* IAM12611 described in Japanese Patent Application Laying-Open (kokai) No. 05-236977, *Candida guilliermondii* NH-2, *Pantoea agglomerans* NH-3 and *Klebsiella pneumoniae* subsp. *pneumoniae* NH-26T2 described in Japanese Patent Application Laying-Open (kokai) No. 05-15384, *Agrobacterium radiobacter* SC-C15-1 described in Japanese Patent Application Laying-Open (kokai) No. 06-14786, *Bacillus smithii* SC-J05-1 described in Japanese Patent Application Laying-Open (kokai) No. 07-25494, *Pseudonocardia thermophila* ATCC19285 described in Japanese Patent Application Laying-Open (kokai) No. 08-56684, and *Pseudonocardia thermophila* JCM3095 described in Japanese Patent Application Laying-Open (kokai) No. 09-275978.

Additionally, the microorganisms of interest according to the present invention also include transformants which may be any host wherein a nitrile hydratase gene cloned from the above microorganisms is expressed.

Preferable examples thereof include MT-10822 bacteria strain (FERM BP-5785) described in U.S. Pat. No. 5,807,730 wherein *Escherichia coli* is used as a typical host.

As a medium substrate, examples of a carbon source include a sugar alcohol represented by the general formula (I) and/or a ketose represented by the general formula (II). Specifically, fructose, mannitol and sorbitol are preferable. These carbon sources can also be used in a suitable combination thereof.

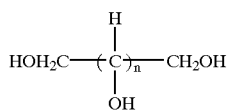

[I]

(wherein n represents an integer from 2 to 4)

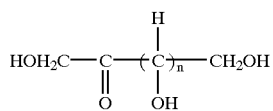

[II]

(wherein n represents 3)

Any supply source of cobalt ion may be employed as long as it is a divalent or trivalent cobalt salt. Examples thereof include cobalt chloride, cobalt sulfate, cobalt acetate, cobalt bromide, and cobalt borate. In addition, vitamin $B_{12}$ or the like may be the cobalt source. Further, the cobalt ion concentration is 15 mg/L or more in terms of $CoCl_2$, preferably 15 to 300 mg/L.

Nitrogen source such as ammonia, ammonium sulfate, ammonium chloride, and ammonium nitrate; organic nutritive source such as yeast extract, meat extract, malt extract, peptones, and Soybean hydrolyzate; and inorganic salts such as phosphates, magnesium salts, potassium salts, sodium salts, iron salts, cobalt salts, and other trace mineral salts, are selected for the preparation of the medium. As needed, an enzyme inducer such as urea or its derivatives may be added.

Further, if necessary, the carbon source, cobalt ions or the like may be added in portions while cultivating.

While cultivating, the pH is to be kept normally at 5 to 10, preferably 7 to 9. The cultivation temperature is normally 25 to 50° C., preferably 30 to 40° C., and the cultivation is aerobically conducted for 1 to 3 days.

BEST MODE FOR CARRYING OUT THE INVENTION

Hereinafter, the present invention will be described more specifically by referring to the following Examples. However, the present invention is not limited to these Examples.

EXAMPLE 1

(1) Cultivating Microbes
① Pre-culture Conditions:
(Medium Composition)
fructose 2% (w/v), polypeptone 5% (w/v) (Nihon Pharmaceutical Co., Ltd.), yeast extract 0.3% (w/v) (Oriental Yeast Co., Ltd.), $KH_2PO_4$ 0.1% (w/v), $K_2HPO_4$ 0.1% (w/v), $MgSO_4$·$7H_2O$ 0.1% (w/v), pH 7
(Culture Method)
100 ml of the medium was dispensed into a 500 ml Erlenmeyer flask and the flask was sealed with a cotton plug. The medium was sterilized by an autoclave for 20 minutes at 121° C. Then, *Rhodococcus rhodochrous* J-1 strain (FERM BP-1478) was inoculated thereto and the mixture was subjected to shake cultivation for 48 hours at 30° C.
② Main Culture Conditions
(Medium Composition)
Initial medium: yeast extract 0.2% (w/v), $KH_2PO_4$ 0.1% (w/v), $K_2HPO_4$ 0.1% (w/v), $MgSO_4$·$7H_2O$ 0.1% (w/v), $CoCl_2$·$6H_2O$ 0.002% (w/v), ammonium sulfate 0.025% (w/v), fructose 2% (w/v), urea 2% (w/v), ethanol 0.4% (v/v), Pluronic L61 0.1% (w/v) (Asahi Denka Kogyo K.K.), pH 7

After-addition medium: fructose 20% (w/v), ethanol 5% (v/v), ammonium sulfate 6% (w/v), pH 6.5
(Culture Method)
Two liters of the initial medium was dispensed into a 3-liter mini jar fermenter (Takasugi Seisakusho) and sterilized by an autoclave for 20 minutes at 121° C. However, apart from the above, fructose, ethanol and urea were aseptically filtrated (using 0.45-micron filter paper manufactured by Advantec Toyo Kaisha, Ltd.) and then added to the medium. After termination of the above pre-culture, 20 ml of the pre-cultivated solution was inoculated thereto and the resultant medium was cultivated for 44 hours at 30° C. under the conditions of an in-tank pressure of 0.098 MPa, a stirring rate of 600 rpm, an airflow quantity of 1 vvm, and pH 7.

In addition, from 20 hours onward after the start of the cultivation, the after-addition medium was added at a flow rate of 20 ml/hr until the end of the cultivation.

(2) Determination of Nitrile Hydratase Activity
0.1 ml of the culture solution and 4.90 ml of 1/20M phosphate buffer solution (pH 7.7) were mixed, and a further 5 ml of 1/20M phosphate buffer solution (pH 7.7) containing 5.0% (w/v) of acrylonitrile was added thereto, and the mixture was then reacted for 10 minute at 10° C. After termination of the reaction, microbial cells were filtered and separated by centrifugation. Acrylamide in the supernatant was quantified by gas chromatography (GC-14B manufactured by Shimadzu Corporation). Analysis was carried out under the following conditions: use of 1 m glass column packed with Porapack PS (column packing material manufactured by Waters Corporation); column temperature of 230° C.; use of FID at 250° C.

Hereinafter, one unit of enzyme activity in the above activity determination is defined as the conversion of 1 μmol of acrylonitrile into acrylamide in 1 minute. With respect to the activity, investigation was carried out per culture solution and per microbial cell. The results are shown in Table 1. In the Table, by taking 100 as the value for activity under the cultivation in the presence of 0.002% (w/v) of $CoCl_2$·$6H_2O$, the activity values under the other culture conditions are indicated as relative activity values (%).

EXAMPLES 2 to 5

Examples 2 to 5 were conducted in the same manner as Example 1, except for using main culture medium to which the following concentrations of CoCl$_2$.6H$_2$O were added instead of 0.002% (w/v) of CoCl$_2$.6H$_2$O: 0.005% (w/v) for Example 2, 0.01% (w/v) for Example 3, 0.02% (w/v) for Example 4, and 0.03% (w/v) for Example 5. The results are shown in Table 1.

EXAMPLES 6 and 7

Examples 6 and 7 were conducted in the same manner as Example 3, except for using both pre-culture and main culture mediums to which mannitol (Example 6) or sorbitol (Example 7) was added instead of fructose. The results are shown in Table 1.

COMPARATIVE EXAMPLE 1

Comparative Example 1 was conducted in the same manner as Example 1, except for using pre-culture and main culture mediums to which glucose was added instead of fructose. The results are shown in Table 1.

COMPARATIVE EXAMPLE 2 to 5

Comparative Examples 2 to 5 were conducted in the same manner as Comparative Example 1, except for using main culture medium to which the following concentrations of CoCl$_2$.6H$_2$O were added instead of 0.002% (w/v) of CoCl$_2$.6H$_2$O: 0.005% (w/v) for Comparative Example 2, 0.01% (w/v) for Comparative Example 3, 0.02% (w/v) for Comparative Example 4, and 0.03% (w/v) for Comparative Example 5. The results are shown in Table 1.

EXAMPLE 8

Example 8 was conducted in the same manner as Example 1, except for using *Nocardia* sp. N-775 strain (deposited as N-755 under the accession No. FERM BP-961) instead of *Rhodococcus rhodochrous* J-1 strain. The results are shown in Table 2.

EXAMPLE 9

Example 9 was conducted in the same manner as Example 8, except for using main culture medium to which 0.01% (w/v) of CoCl$_2$.6H$_2$O was added instead of 0.002% (w/v) of CoCl$_2$.6H$_2$O. The results are shown in Table 2.

EXAMPLES 10 and 11

Examples 10 and 11 were conducted in the same manner as Example 9, except for using pre-culture and main culture mediums to which mannitol (Example 10) or sorbitol (Example 11) was added instead of fructose. The results are shown in Table 2.

COMPARATIVE EXAMPLE 6

Comparative Example 6 was conducted in the same manner as Example 8, except for using pre-culture and main culture mediums to which glucose was added instead of fructose. The results are shown in Table 2.

COMPARATIVE EXAMPLE 7

Comparative Example 7 was conducted in the same manner as Comparative Example 6, except for using main culture medium to which 0.01% (w/v) of CoCl$_2$.6H$_2$O was added instead of 0.002% (w/v) of CoCl$_2$.6H$_2$O. The results are shown in Table 2.

TABLE 1

| | Sugar | CoCl$_2$ Concentration | Activity per microbial cell | Activity per culture solution |
|---|---|---|---|---|
| Example 1 | Fru | 0.002 | 100 | 100 |
| Example 2 | Fru | 0.005 | 215 | 195 |
| Example 3 | Fru | 0.01 | 252 | 229 |
| Example 4 | Fru | 0.02 | 259 | 230 |
| Example 5 | Fru | 0.03 | 259 | 231 |
| Example 6 | Mannitol | 0.01 | 250 | 252 |
| Example 7 | Sorbitol | 0.01 | 259 | 247 |
| Comparative Example 1 | Glc | 0.002 | 100 | 18 |
| Comparative Example 2 | Glc | 0.005 | 100 | 16 |
| Comparative Example 3 | Glc | 0.01 | 48 | 6 |
| Comparative Example 4 | Glc | 0.02 | 37 | 3 |
| Comparative Example 5 | Glc | 0.03 | 7 | 0.2 |

TABLE 2

| | Sugar | CoCl$_2$ Concentration | Activity per microbial cell | Activity per culture solution |
|---|---|---|---|---|
| Example 8 | Fru | 0.002 | 100 | 100 |
| Example 9 | Fru | 0.01 | 207 | 188 |
| Example 10 | Mannitol | 0.01 | 217 | 197 |
| Example 11 | Sorbitol | 0.01 | 230 | 209 |
| Comparative Example 6 | Glc | 0.002 | 83 | 15 |
| Comparative Example 7 | Glc | 0.01 | 55 | 10 |

EXAMPLE 12

(1) Cultivating Microbes
① Pre-culture Conditions
(Medium Composition)
polypeptone 1% (w/v), yeast extract 0.5% (w/v), NaCl 0.5% (w/v), ampicillin.Na 100 μg/ml, pH7 (LB medium)
(Culture Method)
100 ml of the medium was dispensed into a 500-ml Erlenmeyer flask and the flask was sealed with a cotton plug. The medium was sterilized by an autoclave for 20 minutes at 121° C. Then, MT-10822 strain (FERM BP-5785) was inoculated thereto and the mixture was subjected to shake cultivation for 6 hours at 37° C.
② Main Culture Conditions
(Medium Composition)
yeast extract 0.5% (w/v), polypepetone 2% (w/v), NaCl 0.06% (w/v), KCl 0.02% (w/v), MgCl$_2$.6H$_2$O 0.2% (w/v), CoCl$_2$.6H$_2$O 0.002% (w/v), MgSO$_4$.7H$_2$O 0.243% (w/v), fructose 4% (w/v), Pluronic L61 0.02% (w/v), pH 7
(Culture Method)
Two liters of the initial medium was dispensed into a 3-liter mini jar fermenter and sterilized by an autoclave for 20 minutes at 121° C. However, apart from the above, fructose and MgSO$_4$.7H$_2$O were aseptically filtrated (using 0.45-micron filter paper manufactured by Advantec Toyo Kaisha, Ltd.) and then added to the medium. After termination of the above pre-culture, 20 ml of the cultivated solution was inoculated thereto and the resultant medium was cultivated for 12 hours at 37° C. under the conditions of an in-tank pressure of 0.025 MPa, a stirring rate of 800 rpm, an airflow quantity of 1 vvm, and pH 7.
(2) Determination of Nitrile Hydratase Activity
Determination of nitrile hydratase activity was carried out in the same manner as in Example 1 (2). With respect to the activity, investigation was carried out per culture solution and per microbial cell. The results are shown in Table 3. In the Table, by taking 100 as the value for activity under the cultivation in the presence of 0.002% (w/v) of $CoCl_2.6H_2O$, the activity values under the other culture conditions are indicated as relative activity values (%).

EXAMPLE 13

Example 13 was conducted in the same manner as Example 12, except for using main culture medium to which 0.01% (w/v) of $CoCl_2.6H_2O$ was added instead of 0.002% (w/v) of $CoCl_2.6H_2O$. The results are shown in Table 3.

EXAMPLES 14 and 15

Examples 14 and 15 were conducted in the same manner as Example 13, except for using main culture medium to which mannitol (Example 14) or sorbitol (Example 15) was added instead of fructose. The results are shown in Table 3.

COMPARATIVE EXAMPLE 8

Comparative Example 8 was conducted in the same manner as Example 12, except for using main culture medium to which glucose was added instead of fructose. The results are shown in Table 3.

COMPARATIVE EXAMPLE 9

Comparative Example 9 was conducted in the same manner as Comparative Example 8, except for using main culture medium to which 0.01% (w/v) of $CoCl_2.6H_2O$ was added instead of 0.002% (w/v) of $CoCl_2.6H_2O$. The results are shown in Table 3.

TABLE 3

|  | Sugar | $CoCl_2$ Concentration | activity per microbial cell | activity per culture solution |
|---|---|---|---|---|
| Example 12 | Fru | 0.002 | 100 | 100 |
| Example 13 | Fru | 0.01 | 342 | 363 |
| Example 14 | Mannitol | 0.01 | 528 | 113 |
| Example 15 | Sorbitol | 0.01 | 436 | 363 |
| Comparative Example 8 | Glc | 0.002 | 87 | 87 |
| Comparative Example 9 | Glc | 0.01 | 38 | 35 |

INDUSTRIAL APPLICABILITY

Ketose such as fructose, sugar alcohols such as mannitol can reduce growth inhibition caused by cobalt ions in cultivating a microorganism having nitrile hydratase activity. As a result, it is possible to obtain microbial cells having nitrile hydratase enzyme activity within a short period and at a high yield

What is claimed is:

1. A method of cultivating a microorganism having nitrile hydratase production ability in a medium substrate containing a sugar alcohol and/or ketose, and a cobalt ion.

2. The method according to claim 1, wherein the sugar alcohol is represented by the general formula (I):

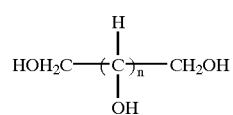

[I]

wherein n represents an integer from 2 to 4.

3. The method according to claim 1, wherein the ketose is represented by the general formula (II):

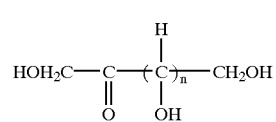

[II]

wherein n represents 3.

4. The method according to claim 1, wherein the concentration of cobalt is 15 mg/L or more in terms of $CoCl_2$.

5. The method according to claim 1, wherein the concentration of cobalt ion is 20 mg/L or more in terms of $CoCl_3$.

* * * * *